US006582384B1

(12) United States Patent
Henry

(10) Patent No.: US 6,582,384 B1
(45) Date of Patent: Jun. 24, 2003

(54) PATIENT WRAPS FOR ARTHROSCOPIC SURGERY AND OTHER USES

(76) Inventor: Barry J. Henry, 2301 89$^{th}$ St., Lubbock, TX (US) 79423

( * ) Notice: Subject to any disclaimer, the term of this patent is extended or adjusted under 35 U.S.C. 154(b) by 201 days.

(21) Appl. No.: 09/228,987

(22) Filed: Jan. 12, 1999

Related U.S. Application Data

(60) Provisional application No. 60/072,288, filed on Jan. 23, 1998.

(51) Int. Cl.[7] .......................... A61F 13/00; A61L 15/00

(52) U.S. Cl. ............................................ 602/75; 602/62

(58) Field of Search ................................ 128/882, 856, 128/DIG. 15, 849–855; 2/69, 912–920, 114; 224/250, 901.4, 158–160; 602/4, 5, 60–62, 75

(56) References Cited

U.S. PATENT DOCUMENTS 3,824,625 A * 7/1974 Green ........................... 2/114
4,787,381 A * 11/1988 Hubbard et al. .......... 602/75 X
5,414,867 A * 5/1995 Bowling et al. ................. 2/51
5,816,253 A * 10/1998 Sosebee .................. 128/852 X
5,916,202 A * 6/1999 Haswell .................. 128/853 X

* cited by examiner

*Primary Examiner*—Denise M. Pothier

(57) ABSTRACT

An apparatus to facilitate a physician's examination and manipulation of a patient's joint which includes an elastic stretchable wrap for wrapping a limb of a patient and for restricting its size to avoid pooling of blood and liquid during manipulation and a surgical garment for the physician, said wrap and garment having cooperating surfaces for affixing the patient's limb to the garment for effecting manipulation of the patient's joint by the surgeon.

5 Claims, 3 Drawing Sheets

10 36 S 70 74 72 38 P 34 22 12 16 28 26 14 18 20 24 72

130a
130b
130c
132

122
122a
122b
124
126

PATIENT WRAPS FOR ARTHROSCOPIC SURGERY AND OTHER USES

Cross Reference. This application claims the benefit of U.S. Provisional Application No. 60/072,288, filed Jan. 23, 1998.

Field of the Invention and Related Art. This invention is directed to the problems of arthroscopic surgery. More particularly, it facilitates the very difficult manipulation requirements of the patient's joints during the arthroscopic surgery.

Illustrative of these difficulties are the manipulations needed to position the arthroscope for examination of all of the compartments of the knee. Such an examination often starts with insertion of the arthroscope through an antero-lateral or anteromedial portal to first examine the lateral or medial gutters. This examination is usually made with the knee being fully extended. Thereafter, the knee must be bent to permit examination of the notch and groove of the femur. Subsequently, varus and valgus forces are applied to the knee to open the medial and lateral joint lines to permit examination of the meniscus.

After examination, remedial repair of the meniscus, the ligaments and tendons may be necessary. Such repair imposes further demands upon the surgeon. For these repairs a surgical instrument is inserted through another portal and both of the surgeon's hands are fully engaged. Similarly, his feet may be needed to actuate and control the speed of motorized instruments such as a shaver. These ambidextrous efforts often require the use of a nurse or surgical assistant to whom various requests for movement of the leg must be made. These requests are for various movements in terms of direction, degree and extent of movement of the extremity. One group of authors has described the problems:

> Manipulation of the knee joint to open and close the various compartments of the knee is critical for adequate visualization of intra-articular structures and successful arthroscopic surgery. For the inexperienced arthroscopist, manipulating the arthroscope and instrument, as well as the knee to provide adequate exposure, can be overwhelming. Therefore, a surgical assistant is usually necessary during arthroscopy of the knee. The surgical assistant stands below the surgeon and manipulates the knee with either varus or valgus stresses in varying degrees of flexion and extension. The surgical assistant is also available to lend a hand when handheld instrumentation is being exchanged or more than two portals are being used.

Fu, Harner and Vince, Knee Surgery, V. 1, p. 550 (Williams and Wilkins, 1994).

The magnitude of these problems is emphasized by the fact that in excess of 400,000 arthroscopic knee surgeries are believed to take place annually within the U.S. Consequently, there are numerous surgeons facing the problem of manipulation daily and many are resorting to the cost and expense of a surgeon's assistant.

The present invention is intended to facilitate these manipulations. In addition, it is intended to minimize or obviate the need for the surgical assistant, to provide more precise positioning of the entire limb, to open the joint further with accuracy while providing excellent control over the extent of the movement so as to minimize the danger of accidental slips with delicate instruments in very delicate spaces. In addition, the invention enables the surgeon to control the pressures exerted on the limb and possibly decrease the incidence of nerve palsies and collateral ligament damage associated with manipulation of the extremity.

Description of the Prior Art. To this inventor's knowledge, the above quotation represents the today's state of the art solution to manipulating the knee during arthroscopic surgery. Such is the only prior method known to him or printed in medical books and journals.

SUMMARY OF INVENTION

This invention is an attaching device for affixing a patient's limb to the surgeon's body for manipulation of the limb and its associated joint or intra-articular structure to facilitate arthroscopic examination or surgery. The invention includes an fastener on the limb and a cooperating fastener carried by the surgeon's body. The fasteners can take many forms. A preferred form is a pressure sensitive fastener such as an adhesive and a bonding surface, the Dual Lock(& fabric fastening system of the 3M Company of St. Paul, Minnesota, etc. More particularly, the preferred pressure sensitive fasteners are those of the traditional hook and loop fasteners such as those sold under the trademark Smart Touch™ by YKK of America and under the Velcro® brand sold by Velcro, USA of Manchester, N.H. Either the hook or loop is formed on a flexible strip that can be wrapped around the limb of the patient with the fastener exposed while the other cooperating fastener is the surface of a surgeon's gown or apron. With the cooperating fasteners being-joined by pressure, the surgeon can easily affix the limb to his gown or apron. In addition, such can be quickly and easily unfastened and affixed to the other side of the apron or gown to facilitate joint manipulation for examination on the opposite side of the joint. In one preferred embodiment, the flexible strip is formed of an elastic fastening material that can be tightly wrapped around the patient's limb for two distinct benefits. The first benefit is a simplistic method of fastening or attaching the limb to the physician's gown or apron for purposes of manipulation, control and stability during the surgery. The second synergistic benefit is that of eliminating the requirement for Coban® or Ace® wrap and the utilization of the elastic fastening material to avoid pooling of blood and fluids within the patient's leg during the surgery.

Accordingly, the objectives of this invention are to provide, among other things, 1) a fastening system for affixing a patient's limb to a surgeon's body to enable the surgeon to accurately manipulate and position the limb's associated joint to facilitate arthroscopic examination and surgery;
2) a pressure sensitive fastening system for affixing a patient's limb to a surgeon's body and to facilitate release and refastening of the limb to a different portion of the surgeon's body for further manipulation;
3) a garment apparatus for arthroscopic examinations that will elimimate the need for a surgeon's assistant and simultaneously facilitate accurate position of the limb and the opening of an intra-articular structure for insertion and examination of the structure;
4) a garment wrap for arthroscopic examinations that will simultaneously serve to prevent the pooling of liquid and blood in a patient's limb and as a fastener device for attaching the garment apparatus and the patient's limb to the surgeon's body;
5) an elastic garment wrap for a patient's limb that will simultaneously serve to prevent or reduce the pooling of liquid and blood in the patient's limb and as a fastener device for affixing the limb to a fixture or a surgeon's body, thereby eliminating the need for Coban or Ace wrappings which performs the single function of preventing pooling of blood;

6) a low cost adhesive device for affixing a patient's limb to a surgeon's body for manipulation thereof; and 7) a simplified arthroscopic surgery method avoids confusion and miscommunications between the surgeon and the assistant as to the angle, height or magnitude of the necessary movement of the limb;

8) elimination or minimization of the need for surgeons assistant to manipulate a patient's limb during surgery;

9) an arthroscopic surgical method and system for decreasing the incidence of nerve palsies and collateral ligament damage as well as damage to other elements of the joint, 10) a low cost wrap for simultaneously preventing the pooling of blood and for fastening a patient's limb to a fixture, support of a surgeon's body; and 11) a low cost garment wrap combination for simultaneously preventing the pooling of blood in a patient's limb, for positioning and affixing said limb to a support, fixture or surgeon's garment and for facilitating arthroscopic surgical examinations.

DESCRIPTION OF THE DRAWINGS

The manner in which these objectives and other desirable characteristics can be obtained from this invention is explained in the following specification and attached drawings in which.

DETAILED DESCRIPTION

Figure 1:
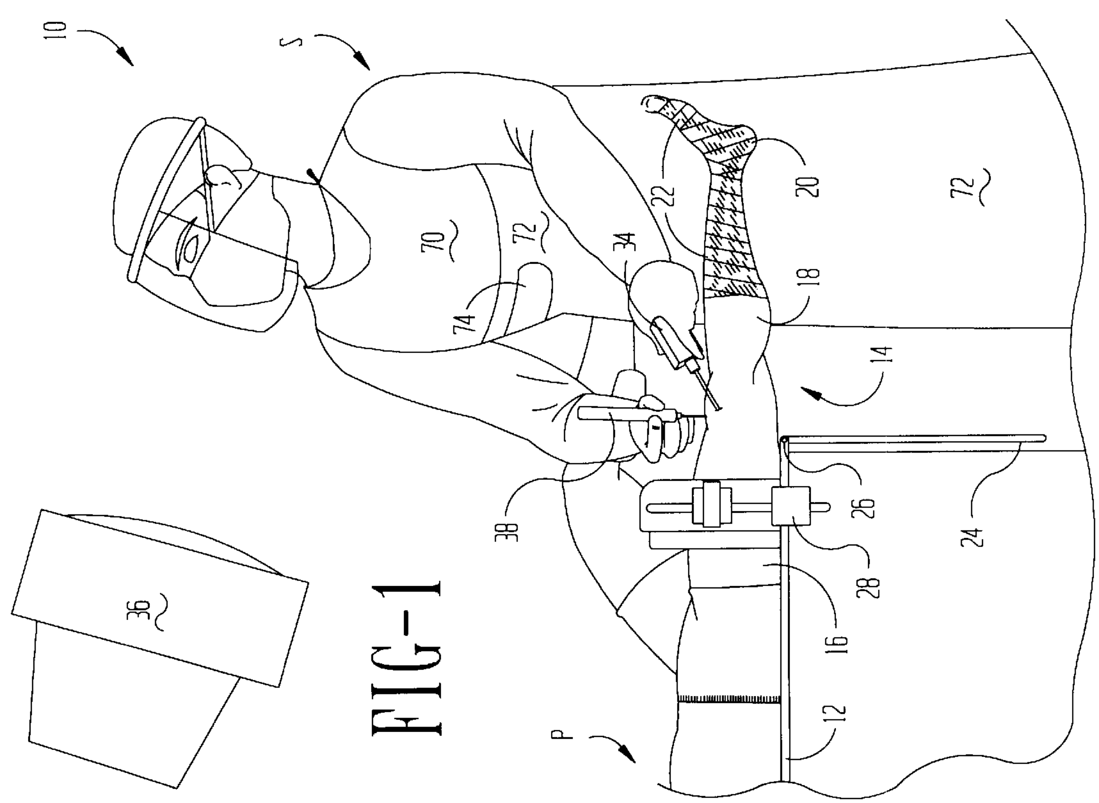
FIG. 1 is a partial plan view of an operating room illustrating a surgeon performing arthroscopic surgery on a patient's knee using a preferred embodiment of this invention.

A preferred embodiment of the present invention is depicted in one intended environment in FIG. 1 of the drawings. This environment is the operating room 10 in which a patient P is undergoing arthroscopic surgery on his right knee 14 by a surgeon S. The patient's leg 18 extends off the operating table. Through a wrapping 22, the patient's foot 20 is affixed to the surgeon's gown 70 having the pressure sensitive fastener system 72 of this invention. When the foot is so affixed, this fastener system permits the supporting plate 24 of the operating table to be pivoted about its hinge 26 to a vertical, non-supporting position and simultaneously gives the surgeon complete control over the positioning of the foot 20, leg 18 and the knee 14. To further assist manipulation of the knee, the patient's thigh 16 is encapsulated in a relatively rigid plastic or foam holder 30 that is affixed to the operating table 12 through a mounting holder or post 28. This holder 28 is conventional and may be used by the surgeon as a fulcrum to manipulate the knee joint.

Figure 2:
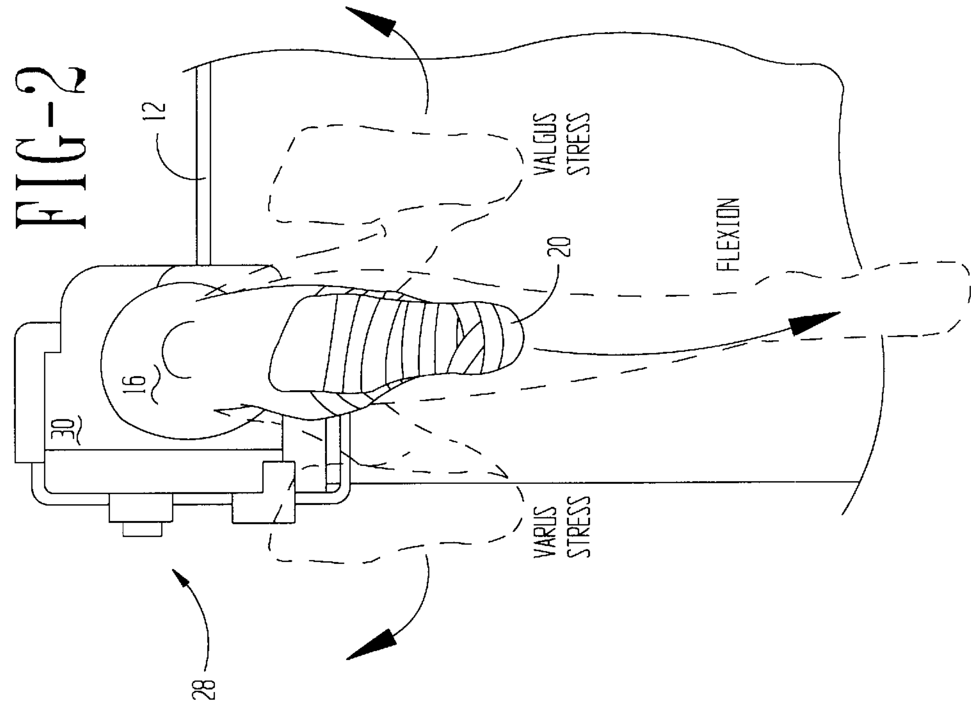
FIG. 2 is a plan view illustrating some of the movements and manipulations required of a leg during arthroscopic surgery.

Before considering the detail construction of the fastening system, its benefits and the problem it solves can best be described in reference to FIGS. 1 and 2. A surgeon often begins arthroscopic examination of the knee 14 in the position generally depicted in FIG. 1, ie., the leg 18 generally straight. In this position, the arthroscope 34 is inserted through a portal into the knee 14 and passed along the medial and lateral gutters (not shown). The camera of the scope is connected to the TV camera 36 to provide the surgeon with a picture of the gutters. Next, the leg 18 is flexed downward approximately 70 degrees to permit the scope to view and examine the grove on the femur (not shown). This flexing of the knee 14 can be effected by the surgeon's body movement in squatting down or, alternatively, he can remove the scope 34, grasp the leg 18 and merely reposition it downward on the fastening system 72 of his gown. With the leg 18 extending downward as shown in the dotted line position of FIG. 2, the notch of the femur can be examined.

Finally with the leg 18 generally straight, as shown in FIG. 2, the surgeon can easily apply a varus stress to the knee 15 by leaning into the leg 18 to fulcrum the knee 14 about the post 28 and its holding member 30. Such will open the lateral side of the knee to facilitate insertion of the scope 34 into the joint line and examination of the meniscus. Alternatively, the surgeon can move the leg 18 to his opposite hip to apply a valgus force to open the medial joint line. Significantly, this body movement and control of the leg 18 and knee 14 eliminates the confusing communications between a surgeon and an assistant. No longer does the assistant have to guess at the desired angle or magnitude of movement of the leg 18, its height or the extent of the desired manipulation. The surgeon, observing the TV and using his body motion, can precisely move the knee 14 and leg 18 until he observes the desired compartment of the joint.

As will be appreciated by those skilled in the art, the fastening system for affixing the patient's limb to the surgeon's body may take many forms. In some instances, a sterile adhesive or a tape applied to the patient's skin will provide a sufficient bonding to a surgeon's gown upon the application of pressure. However, the preferred embodiment of the fastening system is a hook and loop system which may be sold under a brand name such as Velcro® fastener. This preferred fastener system is depicted in FIGS. 4 through 7.

Figure 4:
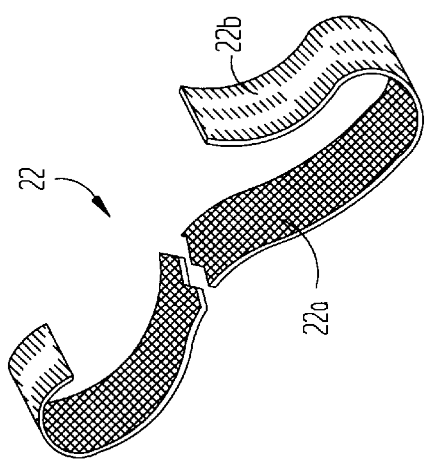
FIG. 4 is a view in perspective of a fastener wrapping for a patient's limb.

FIG. 4 depicts a wrapping formed of Velcro, USA's ONE WRAP™ tape in a width of two inches and having an HTH 22 hook. This fastening tape has a back-to-back fastening system that permits the tape to be wrapped around the leg 18 with some overlap so as to fasten to itself about the leg. Preferably, the loop side **22*a* is positioned adjacent the patients skin and hook side 22*b* is exposed for further fastening or affixation to the apron of FIG. 5 which is formed of a loop material such as L 3610 of Velcro, USA. Many surgeons will find that this ONE WRAP™ tape can be applied rather tightly so as to eliminate the elastic Coban® tape that is normally used to constrict the leg's volume and preclude the pooling of liquid and blood in the leg during surgery. Alternatively, Velcro, USA, as well as others are believed to make an elastic loop tape which can be used as a substitute for the Coban® and thereby further reduce costs. After the leg is wrapped, it is affixed, by the application of pressure, to the surface of gown 72** having a hook structure for manipulation by the surgeon as discussed above.

Figure 5:
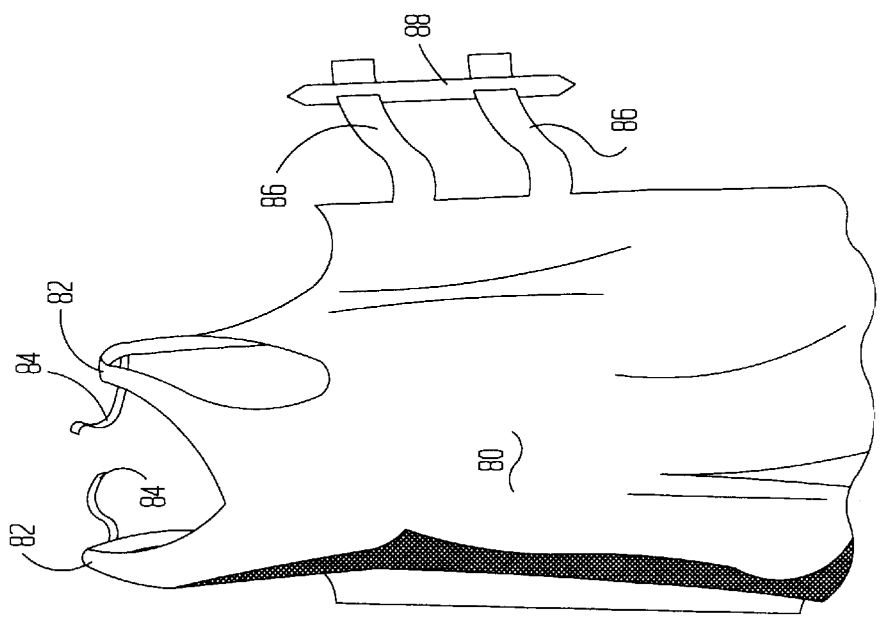
FIG. 5 is perspective view of a preferred embodiment of the surgical apron having a surface of this invention.

One alternative for the gown 72 is the apron 80 of FIG. 5 which takes the general shape of apron with shoulder straps 82 which can be interconnected by a cross straps 84 of hook and loop material to hold the shoulder straps in place. Just below the waist of the surgeon are two apron strings 86 formed of a hook material for passing around the surgeon and locking to the hoop material of the apron skirt. Preferably a cardboard holder 88 is placed on the strings for shipping and for wrapping about the physician by a scrub nurse without affecting the sterility of the strings.

Figure 3:
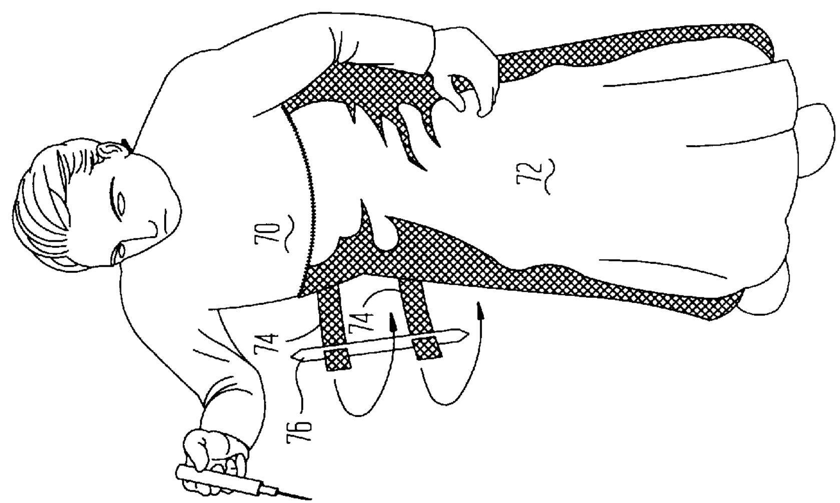
FIG. 3 is a perspective view of a surgical gown having a fastener surface of this invention bonded or otherwise affixed to the surgical gown.

In the event that the apron 80 of FIG. 5 is utilized, it will be worn over the traditional surgical gown (not shown). Alternatively, the embodiment of FIG. 3 depicts a gown 70 in which the skirt 72 is formed of the loop material which is attached to the gown 70. For example, the fastening skirt 72 may be sewn or ultrasonically welded to the gown, affixed. thereto by pressure sensitive adhesives, etc. Since loop material is not normally impervious to liquids, the material of the surgeon's gown may be used as a backing.

Figure 7:
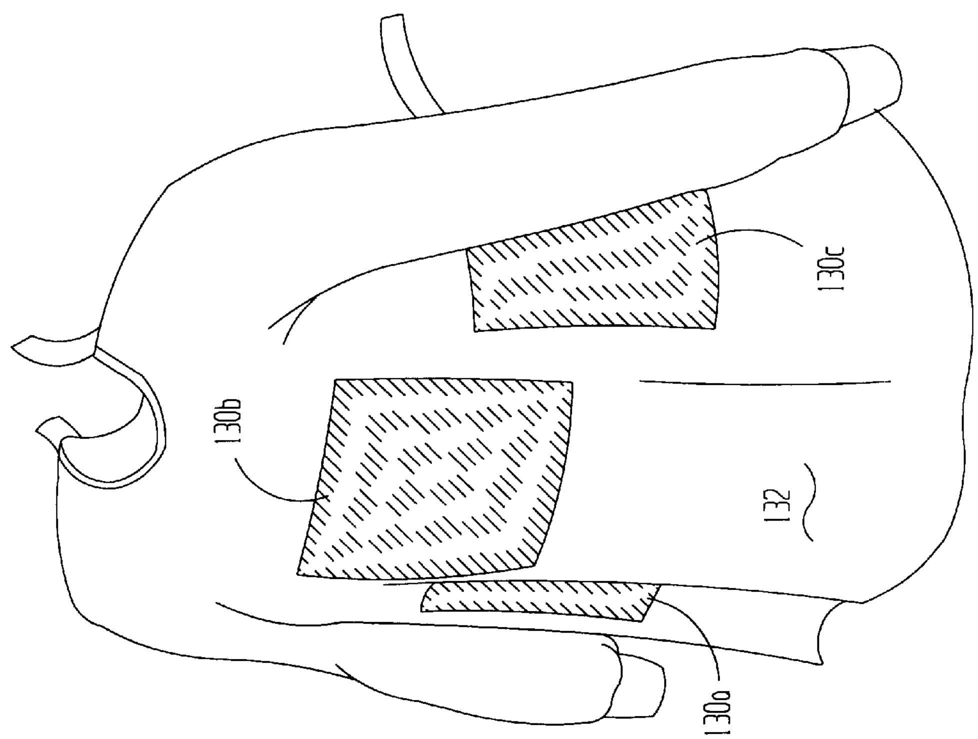
FIG. 7 is a perspective view of a low cost surgeon's gown for facilitating arthroscopic surgeries.
Figure 6:
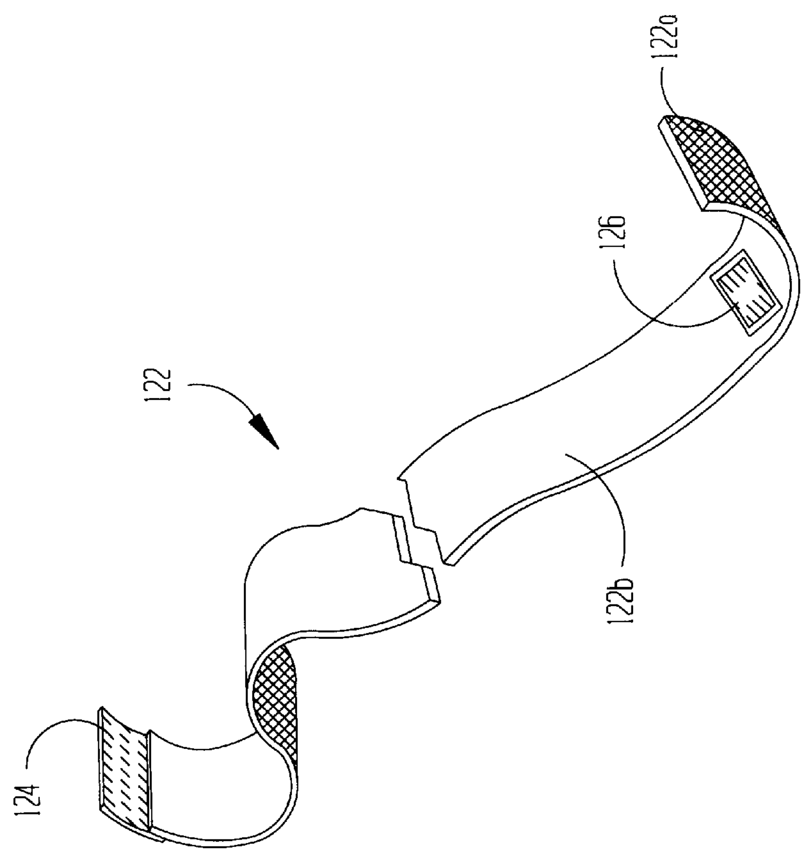
FIG. 6 is a perspective view of another preferred embodiment of an elastic fastening wrap for wrapping a patient's limb to prevent the pooling of blood and the affixation of the limb to a support or a surgeon's garment.

Those skilled in the art will appreciate that this invention may take many forms and that the preferred embodiment is subject to various modifications. For example, the hook and loop material may be reversed with the hook material being used as the apron 80 or the skirt 72 of gown 70. One such alternative is depicted in FIGS. 6 and 7. This embodiment may be preferred where the primary consideration is one of costs.

As shown in FIG. 6, the wrap 122 is formed of a stretchable, elastic loop material for wrapping the patient's leg. A preferred material is that sold by Velcro, USA of Manchester, N.H. under the designation "MED FLEX." With the smooth side 122*b* being placed against the patient's skin, this material is stretched and wrapped around the leg 22 to eliminate the need for the Coban® or Ace® wraps that are normally used to prevent swelling and pooling of blood and fluids in the leg. In addition to prevention of pooling of fluid, the wrapping has a loop structure 122*a* which is remains exposed after the wrapping. This loop structure permits a pressure sensitive affixation of the leg to the surgeon's gown depicted in FIG. 7.

The gown of FIG. 7 is a standard surgical gown such as that manufactured and sold by Allegiance Healthcare Corporation of McGaw Park, Ill. 60085 under the catalog designation 9575. Affixed to this gown are preferably three generally rectangular segments of hook material 130(*a*), 130(*b*) and 130(*c*). Preferably this material is one such as that sold as HTH 805 having a 0115 adhesive affixed thereto. Such permits the individual segments to be cut into the desired shape. The adhesive backing can then be removed from the adhesive for bonding to the gown 132 in the position shown. It is believed that such a gown with the three hook segments bonded thereto provide adequate control to the surgeon.

In the wrapping depicted in FIG. 6, a hook tab 124 can be can be stitched thereto for locking to the loop structure after the wrapping of the leg. In addition, another hook piece, 126 can be affixed to the wrap 122 to avoid unravelling.

Those skilled in the art will also appreciate alternative pressure sensitive fastening systems. For example, some may prefer the Dual Lock® fabric fastening system of the 3M Company of St. Paul, Minn. Others will find that certain sterile adhesives may be used, particularly for short duration arthroscopic examinations. Moreover, depending upon the expected weight of the patient's leg, a stronger hook and loop systems may be substituted. Numnerous such alternatives will provide acceptable control and manipulation the patient's limbs and joints so as to achieve the benefits of my invention. As known to those skilled in the art, the garment may be sterilized by conventional methods, including the use of ethylene oxide or gamma irradiation.

I claim:

1. An apparatus for facilitating a physician's arthroscopic examination of a patient's joint and careful, precise manipulation of the joint by the surgeon so as to open and close the various compartments of the joint while permitting adequate visualization of the intra-articular structures, said apparatus comprising:

a) a pliable wrap member for a limb of the patient;

b) a surgical garment having at least one cooperating surface member adapted to be worn by a surgeon performing the arthroscopic examination, and c) said members having pressure sensitive surfaces for engaging one another an for affixing the patient's limb to a plurality of positions on the garment for careful manipulation of the joint by the surgeon and in which the wrap member for the extremity of the patient's limb has elastic properties for also constricting the limb and limiting the pooling of blood and liquid in said limb during examination.

2. A flexible material for controlling the positioning of a patient's limb and for restricting swelling and the pooling of fluids in the limb resulting from surgery, said material comprising:

a) an elongated strip of stretchable, elastic material adapted to be wrapped about the limb to constrict its size and to restrict swelling and pooling of fluids in the limb; and b) said strip having a pressure sensitive surface for fixation to another surface for controlling the position of the limb, and a tab having a hook surface which is affixed to said strip for engaging said pressure sensitive surface and maintaining it in a stretched, restricting position about a patient's limb.

3. An apparatus for facilitating examination and manipulation of patient's joint so as to open and close the various compartments of the joint while permitting adequate visualization of the intra-articular structures, said apparatus comprising:

a) an elastic member adapted to stretchably wrap a limb of a patient and to restrict it size to avoid pooling and swelling thereof;

b) a garment adapted to be worn by a surgeon having a cooperating surface member adapted to be joined to said elastic member for positioning of said limb;

c) said members having a pressure sensitive surfaces for engaging and affixing the patient's limb to a plurality of positions on the garment adapted to be worn by the surgeon for manipulation of the limb by the surgeon.

4. An apparatus as recited in claim 3 in which one of said pressure sensitive surface comprises a loop structure for fixation to the other surface member.

5. An apparatus as recited in claim 3 in which said surfaces comprise hook and loop surfaces.

* * * * *